United States Patent [19]

Hill et al.

[11] 4,374,136
[45] Feb. 15, 1983

[54] PYRIMIDINE DERIVATIVES

[75] Inventors: Jack Hill, London; Brian W. Sharp, Hornchurch; Dennis Warburton, Brentwood, all of England; Robert B. Walker, deceased, late of Hornchurch, England; by Thomas Walker, administrator, Chester, England

[73] Assignee: May & Baker Limited, Essex, England

[21] Appl. No.: 313,493

[22] Filed: Oct. 21, 1981

[30] Foreign Application Priority Data

Oct. 27, 1980 [GB] United Kingdom ................ 8034572

[51] Int. Cl.³ .................. C07D 239/48; A61K 31/305
[52] U.S. Cl. ...................................... 424/251; 544/298
[58] Field of Search ........................ 544/298; 424/251

[56] References Cited

U.S. PATENT DOCUMENTS 4,179,562 12/1979 Ponsford ............................. 544/298

Primary Examiner—Robert Gerstl
Attorney, Agent, or Firm—Stevens, Davis, Miller & Mosher

[57] ABSTRACT

Compounds of the formula:

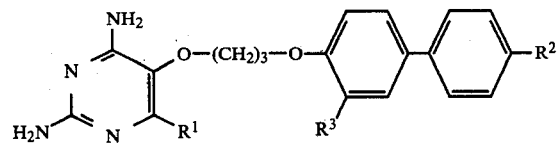

wherein $R^1$ represents a methyl or ethyl group, $R^2$ represents a bromine or chlorine atom, and $R^3$ represents a hydrogen, chlorine, bromine or iodine atom, an alkyl or alkenyl group containing up to 4 carbon atoms, or a cyano or trifluoromethyl group, are new compounds possessing antimalarial properties.

6 Claims, No Drawings

PYRIMIDINE DERIVATIVES

DESCRIPTION

The invention relates to new pyrimidine derivatives, to a process for their preparation, to compositions containing them, and to their use as pharmaceuticals.

British patent specification No. 1546937 discloses inter alia that 2,4-diaminopyrimidine derivatives of the general formula:

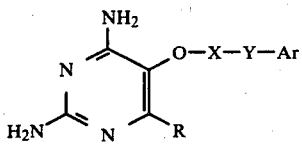

(wherein R represents a hydrogen atom or a methyl or ethyl group, X represents an alkylene group of 1 to 10 carbon atoms, Y represents an oxygen or sulphur atom or a bond, and Ar represents an optionally substituted aryl group, except that Ar-Y-X does not represent a benzyl group when R represents a hydrogen atom) and pharmaceutically acceptable acid addition salts thereof have antimicrobial activity, more particularly antimalarial and antibacterial activity. The aforementioned British patent specification No. 1546937 includes the statement "Suitable groups Ar include phenyl, naphthyl, anthranyl, phenanthryl and phenyl substituted by from 1 to 5 atoms or groups selected from fluorine, chlorine, bromine, lower alkoxyl, lower acyloxyl, lower alkyl, lower alkenyl, $C_{5-6}$ cycloalkyl, $C_{5-6}$ cycloalkenyl or lower alkylthio. When used herein the term 'lower' means that the group contains up to 6 carbon atoms," and the following values of Ar appear in the Examples: cyclohexyl-chloro-phenyl, dichlorophenyl, naphthyl, phenanthryl, pentachlorophenyl, tetrachlorophenyl, trichlorophenyl, propenylbromo-phenyl, bromophenyl, propenyl-methoxy-phenyl, trimethoxyphenyl, dimethoxyphenyl, methoxyphenyl, ethylthiophenyl, phenyl, and chlorophenyl.

British patent specification No. 1546937 does not mention or disclose biphenyl or substituted biphenyl as a possible value for symbol Ar in any part, including the Examples and Claims.

It has now unexpectedly been found that, related in structure to the millions of compounds within the scope described in detail in British patent specification No. 1546937, there are a small group of substituted biphenyl compounds which are of particularly outstanding utility as antimalarials.

Accordingly, the present invention provides pyrimidine derivatives of the general formula:

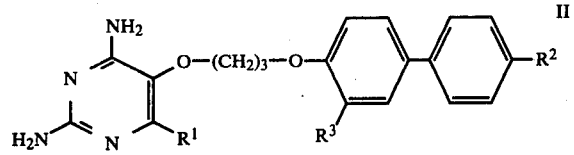

(wherein $R^1$ represents a methyl or ethyl group, $R^2$ represents a bromine or chlorine atom, and $R^3$ represents a hydrogen, chlorine, bromine or iodine atom, a straight- or branched-chain alkyl or alkenyl group containing up to 4 carbon atoms, or a cyano or trifluoromethyl group) and pharmaceutically acceptable acid addition salts thereof.

The compounds of formula II are much more active as antimalarials than the compounds particularly described in British patent specification No. 1546937 (hereinafter referred to for convenience as "the compounds of B.P. 1546937"), and this is especially important against strains of malarial infections which are resistant to known antimalarial agents. The compounds of formula II are also less toxic than the compounds of B. Pat. No. 1546937. This surprising advantage in antimalarial therapeutic index is particularly remarkable because the compounds of formula II are of no activity, or of only low activity, as antibacterials. Indeed, this constitutes another advantage for the compounds of formula II because antimalarial compounds are commonly administered over a long period for their prophylactic effect. Many medical practitioners prefer not to administer antibacterial compounds over extended periods because of the risk of developing resistant strains of bacteria. The compounds of formula II may be administered continuously with no danger of developing resistant strains of bacteria.

A particularly preferred compound of formula II is 2,4-diamino-5-[3-{4-(4-chlorophenyl)phenoxy}propoxy]-6-methylpyrimidine of formula:

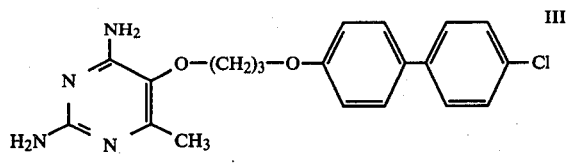

and pharmaceutically acceptable acid addition salts thereof. Another preferred compound of formula II is 2,4-diamino-5-[3-{2-bromo-4-(4-bromophenyl)phenoxy}-propoxy]-6-methylpyrimidine of formula:

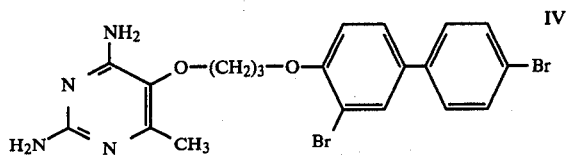

and pharmaceutically acceptable acid addition salts thereof.

By the term "pharmaceutically acceptable acid addition salts" as used in this specification is meant acid addition salts the anions of which are relatively innocuous to the animal organism when used in therapeutic doses so that the beneficial pharmaceutical properties of the parent compounds of formula II are not vitiated by side-effects ascribable to those anions.

As well as being useful in themselves as active compounds, acid addition salts of the compounds of formula II are useful for the purposes of purification of the parent compounds of formula II, for example by exploitation of the solubility differences between the salts and the parent compounds, by techniques well known to those skilled in the art. The parent compounds of formula II can be regenerated from their acid addition salts by known methods, for example by treatment with an alkali, e.g. aqueous sodium bicarbonate solution or aqueous ammonia solution.

Suitable acid addition salts for use in pharmaceuticals may be selected from salts derived from inorganic acids, for example hydrochlorides, hydrobromides, phosphates, sulphates and nitrates, and organic acids, for example oxalates, lactates, tartrates, acetates, salicylates, citrates, propionates, succinates, fumarates, maleates, methylene-bis-β-hydroxynaphthoates, gentisates and di-p-toluoyltartrates.

According to a feature of the present invention, the compounds of formula II may be converted to their acid addition salts by known methods, for example, by reaction with the appropriate acid in solution in a suitable solvent, e.g. ethanol, followed if necessary by evaporation of part or all of the solvent, and collection of the solid salt.

It is to be understood that, where in this specification reference is made to the compounds of formula II, it is intended to refer also, where the context so permits, to acid addition salts of the compounds of formula II.

By the term "known methods" as used in this specification is meant methods heretofore used or described in the literature.

According to a feature of the present invention, the compounds of formula II are prepared by the process which comprises the reaction of a 2,4-diamino-5-hydroxy-6-alkylpyrimidine of the general formula:

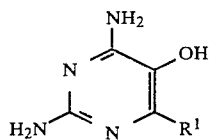

(wherein R¹ is as hereinbefore defined) or a basic salt thereof, for example an alkali metal (e.g. sodium or potassium) salt, with a biphenyloxypropyl compound of the general formula:

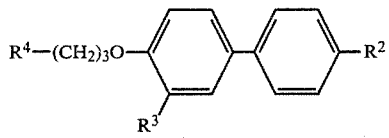

wherein R⁴ represents the acid residue of a reactive ester, for example a halogen (e.g. bromine or chlorine) atom or a p-tolylsulphonyl or methylsulphonyl group, and R² and R³ are as hereinbefore defined. The reaction is preferably carried out in a polar solvent medium, for example in a mixture of tetrahydrofuran and methanol, and optionally at an elevated temperature, for example the reflux temperature of the reaction mixture.

The compounds of formula V may be prepared by the methods described by R. Hull, Journal of the Chemical Society, (1956), 2033.

Compounds of formula VI may be prepared by the application or adaptation of known methods.

According to a feature of the present invention, the compounds of formula II may be used to treat malaria.

The compounds of formula II are especially useful in the treatment of malaria, as they are able effectively to treat malarial infections which are resistant to known antimalarial agents. The compounds of formula II can be used alone or in association with other therapeutic agents and, in some circumstances, mixtures of the compounds of formula II with other antimalarial compounds have antimalarial activities which are much higher than could be expected from mere arithmetic addition of the activities of the individual components of the mixture, and this is especially important against malarial infections which are resistant to other antimalarial compounds. Good examples of other therapeutic agents which may be used in association with the compounds of formula II include sulphonamides, e.g. sulphadiazine [i.e. 2-sulphanilamidopyrimidine], sulphadoxine [i.e. 5,6-dimethoxy-4-sulphanilamidopyrimidine], sulphadimethoxine [i.e. 2,6-dimethoxy-4-sulphanilamidopyrimidine] and sulphalene [i.e. 2-methoxy-3-sulphanilamidopyrazine], and sulphones, for example dapsone [i.e. bis(4-aminophenyl) sulphone].

The usefulness of the compounds of formula II is enhanced by the fact that they have a toxicity in mammals which is moderately low.

The properties of the compound of formula III are illustrated by the following laboratory tests. Similar tests were carried out on 35 of the 39 specifically described compounds of B.P. 1546937 and one compound, 2,4-diamino-6-methyl-5-[3-(4-chloro-2-cyclohexylphenoxy)propoxy]pyrimidine (hereinafter referred to as "reference compound RCA") was found to be at least 4 times as active against malaria as any of the other 34 compounds. The test results for reference compound RCA are given for comparison with those for the compound of formula III, and it is clear that the compound of formula III is very much more active than reference compound RCA against sensitive and resistant strains of malaria and, furthermore, that the compound of formula III is much less toxic in dogs than reference compound RCA.

The other compounds of formula II, for example the compound of formula IV, have similar advantages over reference compound RCA and the other compounds of B.P. 1546937.

Antimalarial activity (a) The test compounds were tested in mice, against *Plasmodium yoelii nigeriensis* (strain N67), which is sensitive to pyrimethamine, and against a strain of *Plasmodium yoelii nigeriensis* [strain PR (derived from strain N67)] which is resistant to pyrimethamine, and also against pyrimethamine sensitive *Plasmodium berghei* (strain N30).

Pyrimethamine [i.e. 2,4-diamino-5-(4-chlorophenyl)-6-ethylpyrimidine] is an antimalarial compound which is an article of commerce.

In the experiments, the mice were each infected intraperitoneally with about 10⁶ trophozoites. The test compound was administered orally daily for 4 days, beginning on the day of infection, and peripheral blood smears of the mice were observed 2 or 3 times per week for a total of 21 days. The numbers of mice cured were counted and the dose required to cure 50% of mice tested (CD50) was calculated.

The results obtained are shown below in Table I.

TABLE I

| Test Compound | Strain | Daily dose mg/kg | Number of mice tested | Number of mice cured | CD50 mg/kg/day |
|---|---|---|---|---|---|
| The compound of formula III | N67 | 2.0 | 31 | 31 | 0.3 |
| | | 0.5 | 32 | 28 | |
| | | 0.125 | 32 | 2 | |
| | PR | 20.0 | 15 | 15 | 3.0 |
| | | 2.0 | 16 | 3 | |
| | | 0.2 | 16 | 0 | |
| | | 2.0 | 24 | 24 | |

TABLE I-continued

| Test Compound | Strain | Daily dose mg/kg | Number of mice tested | Number of mice cured | CD50 mg/kg/ day |
|---|---|---|---|---|---|
| | N30 | 0.5 | 24 | 14 | 0.45 |
| | | 0.125 | 24 | 0 | |
| | | 25 | 31 | 31 | |
| | N67 | 5 | 32 | 17 | 5 |
| | | 1 | 32 | 2 | |
| Reference compound RCA | PR | 100 | 32 | 32 | 30 |
| | | 10 | 32 | 0 | |
| | | 100 | 24 | 24 | |
| | N30 | 10 | 24 | 5 | 15 |
| | | 1 | 24 | 0 | |

(b) Mice were each infected intraperitoneally with about $10^6$ trophozoites of strain N67 of *Plasmodium yoelii nigeriensis*. The compound of formula III was administered orally in one single dose given 48 hours after infection, and the mice were observed for a total of 21 days. The numbers of mice cured were counted and the dose required to cure 50% of mice tested (CD50) was calculated.

The results obtained are shown below in Table II, in comparison with a test using pyrimethamine against the same organism.

TABLE II

| Compound | Dose mg/kg | Number of mice tested | Number of mice cured | CD50 mg/kg |
|---|---|---|---|---|
| The compound of formula III | 20.0 | 8 | 8 | |
| | 2.0 | 8 | 1 | 3.5 |
| | 0.2 | 8 | 0 | |
| | 50.0 | 8 | 0 | |
| pyrimethamine | (maximum tolerated dose) 5.0 | 8 | 0 | greater than 50 |

In comparison an oral dose of 200 mg/kg of reference compound RCA was administered to each of 8 mice 24 hours after infection, and only 2 mice were cured, giving a CD50 of greater than 200 mg/kg.

It is to be noted that administration of an antimalarial drug 24 hours after infection should generally be more efficacious than administration 48 hours after infection.

Toxicity

Acute oral toxicity in mice

Mice were treated with a single dose of the compound of formula III by the oral route, and were observed until all survivors had appeared to be healthy for 3 consecutive days. The LD50 dose (dose required to kill 50% of the mice tested) was then calculated. The results obtained are shown below in Table III.

TABLE III

| Dose mg/kg | Number of mice tested | Number of mice killed | LD50 mg/kg |
|---|---|---|---|
| 1000 | 5 | 3 | approximately 1000 |
| 500 | 5 | 0 | |

In a similar test on reference compound RCA an oral dose of 1000 mg/kg killed 2 out of 5 mice, giving an LD50 figure of approximately 1000 mg/kg.

Toxicity in dogs

The compound of formula III was found to be clinically well-tolerated by dogs when administered orally in gelatin capsules for a period of one month at dosages of 1, 3 and 9 mg/kg/day. The compound of formula III was also clinically well-tolerated by 5 of the 6 dogs which received the highest dosage of 15 mg/kg/day.

In contrast, reference compound RCA was found to be clinically badly tolerated even at doses of 3 mg/kg/day, with deaths occurring at higher doses.

The following Examples illustrate the preparation of the compounds of the present invention.

EXAMPLE 1

2,4-Diamino-5-hydroxy-6-methylpyrimidine dihydrogen sulphate (137.5 g) was added to a stirred solution of sodium methoxide [prepared by dissolving sodium (39.8 g) in anhydrous methanol (2350 ml)]. The stirred mixture was heated at reflux for 30 minutes and then for a further 150 minutes during the gradual addition of a solution of 3-[4-(4-chlorophenyl)-phenoxy]propyl bromide (188 g) in anhydrous tetrahydrofuran (940 ml) and then the mixture was stirred and heated at reflux for a further 18 hours. Part of the solvent (approximately 2400 ml) was removed by distillation at atmospheric pressure and the remaining mixture was diluted with water (3000 ml). The resulting suspension was cooled to 40° C., and the solid was filtered off, washed well with water and dried at 85° C. The solid was then dissolved in hot dimethylformamide (1000 ml) and the resulting solution was filtered through diatomaceous earth and treated, successively, with concentrated hydrochloric acid (50 ml) and acetone (2000 ml). The resulting suspension was cooled to 10° C. and filtered, and the solid was washed well with acetone to give 2,4-diamino-5-[3-{4-(4-chlorophenyl)phenoxy}propoxy]-6-methylpyrimidine monohydrochloride (178 g), m.p. 263°–265° C. (with slight decomposition).

Elemental analysis: C, 57.1; H, 5.2; Cl, 16.6; N, 13.2%; $C_{20}H_{22}Cl_2N_4O_2$ requires C, 57.0; H, 5.3; Cl, 16.8; N, 13.3%.

3-[4-(4-Chlorophenyl)phenoxy]propyl bromide of formula VI, used as a starting material, was prepared as follows:

A methanolic solution of sodium methoxide prepared by dissolving sodium (35.7 g) in anhydrous methanol (300 ml) was treated with 4-(4-chlorophenyl)-phenol (311 g) and the resulting solution was added to a stirred solution of 1,3-dibromopropane (850 ml) in anhydrous methanol (500 ml) at reflux during a period of 6 hours. The mixture was stirred at reflux for a further period of 18 hours and was then evaporated to dryness in vacuo. The crystalline residue was triturated with petroleum ether (b.p. 40°–60° C.), filtered off and dried, and was then triturated with aqueous potassium hydroxide solution (1500 ml; 5% w/v), filtered off, washed well with water and dried. The solid was subjected to fractional crystallisation from a mixture of isopropanol and acetone. The first crop was discarded. The second crop (161 g) was dissolved in acetone, filtered, and evaporated. The third crop (53 g) was recrystallised from ethanol. The fourth crop was recrystallised from isopropanol and then twice from ethanol. The purified second, third and fourth crops were combined and dissolved in acetone, and the solution was filtered through diatomaceous earth. It was concentrated in vacuo to a volume of 300 ml and was then diluted with a mixture of methanol (200 ml) and water (500 ml). The resulting solid was filtered off and washed with water to give 3-[4-(4-chlorophenyl)phenoxy]propyl bromide (194 g), m.p. 103°–105° C.

EXAMPLE 2

By proceeding in a manner similar to that described in Example 1 but replacing the 3-[4-(4-chlorophenyl)phenoxy]propyl bromide used as a starting material by the appropriate quantities of the corresponding biphenyloxypropyl bromides of formula VI, there were prepared the following compounds, which were crystallised from the solvents indicated:

2,4-diamino-5-[3-{2-bromo-4-(4-bromophenyl)phenoxy}-propoxy]-6-methylpyrimidine monohydrochloride, m.p. 255°–257° C. (from a mixture of dimethylformamide and acetone), and 5-[3-{2-allyl-4-(4-chlorophenyl)phenoxy}propoxy]-2,4-diamino-6-methylpyrimidine monohydrochloride, m.p. 241°–243° C. (from methanol).

By again proceeding in a similar manner to that described in Example 1 but omitting the treatment with hydrochloric acid and using the appropriate biphenyloxypropyl bromides of formula VI, the following compounds were obtained as free bases and crystallised from the solvents indicated:

2,4-diamino-5-[3-{4-(4-bromophenyl)phenoxy}-propoxy]-6-methylpyrimidine, m.p. 198°–200° C. (from a mixture of tetrahydrofuran and ethyl acetate);

2,4-diamino-5-[3-{2-chloro-4-(4-chlorophenyl)phenoxy}-propoxy]-6-methylpyrimidine, m.p. 191°–193° C. (from a mixture of dimethylformamide and tetrahydrofuran);

2,4-diamino-5-[3-{2-bromo-4-(4-chlorophenyl)phenoxy}-propoxy]-6-methylpyrimidine, m.p. 178°–180° C. (from a mixture of dimethylformamide and methanol);

2,4-diamino-5-[3-{4-(4-chlorophenyl)-2-methylphenoxy}-propoxy]-6-methylpyrimidine, m.p. 207°–209° C. (from a mixture of dimethylformamide and acetone);

2,4-diamino-5-[3-{4-(4-chlorophenyl)-2-ethylphenoxy}-propoxy]-6-methylpyrimidine, m.p. 144°–146° C. (from a mixture of dimethylformamide and ethanol);

2,4-diamino-5-[3-{4-(4-bromophenyl)-2-ethylphenoxy}-propoxy]-6-methylpyrimidine, m.p. 146°–148° C. (from a mixture of dimethylformamide and ethanol);

2,4-diamino-5-[3-{4-(4-chlorophenyl)-2-iodophenoxy}-propoxy]-6-methylpyrimidine, m.p. 172.5°–173.5° C. (from a mixture of dimethylformamide and acetone);

2,4-diamino-5-[3-{2-tert-butyl-4-(4-chlorophenyl)phenoxy}propoxy]-6-methylpyrimidine hydrate, m.p. 165°–166° C. (from methanol):
elemental analysis: C, 64.5; H, 6.8; Cl, 7.8; N, 12.9; $H_2O$, 1.9%; $C_{24}H_{29}ClN_4O_2:0.5H_2O$ requires C, 64.3; H, 6.75; Cl, 7.9; N, 12.5; $H_2O$, 2.0%;

2,4-diamino-5-[3-{4-(4-chlorophenyl)-2-iso-propylphenoxy}-propoxy]-6-methylpyrimidine ethanolate, m.p. 140°–144° C. (from a mixture of dimethylformamide and ethanol):
elemental analysis: C, 64.0; H, 6.9; Cl, 7.7; N, 12.5; $—OC_2H_5$, 5.8%; $C_{23}H_{27}ClN_4O_2:0.5C_2H_5OH$ requires C, 64.1; H, 6.7; Cl, 7.9; N, 12.5; $—OC_2H_5$, 5.8%;

2,4-diamino-5-[3-{2-butyl-4-(4-chlorophenyl)phenoxy}-propoxy]-6-methylpyrimidine ethanolate, m.p. 129°–131° C. (from ethanol):
elemental analysis: C, 64.9; H, 7.1; Cl, 7.4; N, 11.8%; $C_{24}H_{29}ClN_4O_2:0.8C_2H_5OH$ requires C, 64.9; H, 7.1; Cl, 7.4; N, 11.7%;

2,4-diamino-5-[3-{4-(4-chlorophenyl)-2-trifluoromethylphenoxy}propoxy]-6-methylpyrimidine ethanolate, m.p. 145°–148° C. (from a mixture of dimethylformamide and ethanol):
elemental analysis: C, 55.1; H, 5.2; Cl, 6.6; F, 11.5; N, 11.6%; $C_{21}H_{20}ClF_3N_4O_2:C_2H_5OH$ requires C, 55.4; H, 5.25; Cl, 7.1; F, 11.4; N, 11.2%;

2,4-diamino-5-[3-{4-(4-chlorophenyl)-2-propylphenoxy}-propoxy]-6-methylpyrimidine, m.p. 106°–108° C. [from a mixture of petroleum ether (b.p. 60°–80° C.) and toluene], and 2,4-diamino-5-[3-{4-(4-chlorophenyl)-2-cyanophenoxy}-propoxy]-6-methylpyrimidine hydrate, m.p. 231°–232° C. (from a mixture of dimethylformamide and acetone):
elemental analysis: C, 60.2; H, 4.8; Cl, 8.3; N, 16.4; $H_2O$, 1.4%; $C_{21}H_{20}ClN_5O_2:0.4H_2O$ requires C, 60.5; H, 5.0; Cl, 8.5; N, 16.8; $H_2O$, 1.7%.

By proceeding in a similar manner to that described in Example 1 but replacing the 2,4-diamino-5-hydroxy-6-methylpyrimidine dihydrogen sulphate, used as a starting material, by the appropriate quantity of 2,4-diamino-6-ethyl-5-hydroxypyrimidine dihydrogen sulphate, there was prepared
2,4-diamino-5-[3-{4-(4-chlorophenyl)phenoxy}-propoxy]-6-ethylpyrimidine monohydrochloride, m.p. 261°–263° C.

The present invention includes within its scope pharmaceutical compositions which comprise at least one compound of formula II in association with a pharmaceutically acceptable carrier or coating, and optionally together with one or more other antimalarial compounds or other therapeutic agents. In clinical practice the compositions of the present invention will normally be administered orally, rectally or parenterally.

Solid compositions for oral administration include compressed tablets, pills, dispersible powders, and granules. In such solid compositions the active compound or compounds are mixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically acceptable emulsions, solutions, suspensions, and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing the active compound or compounds with or without the addition of diluents or excipients.

Solid compositions for rectal administration include suppositories formulated in manner known per se and containing the active compound or compounds.

Preparations according to the invention for parenteral administration include sterile aqueous or non-aqueous solutions, suspensions, or emulsions. Examples of non-aqueous solvents or suspending media are propylene glycol, vegetable oils such as olive oil, and injectable organic esters such as ethyl oleate. These compositions may also contain adjuvants such as preserving, wetting, emulsifying and dispersing agents. They may be sterilised, for example, by filtration through a bacteria-retaining filter, by incorporation of sterilising agents in the compositions, by irradiation, or by heating. They may also be manufactured in the form of sterile solid compositions, which can be dissolved in a sterile injectable medium immediately before use.

The percentages of active ingredients in the compositions of the invention may be varied, it being necessary that they should constitute a proportion such that a suitable dosage for the desired antimalarial effect shall be obtained. Obviously several unit dosage forms may be administered at about the same time. Generally the compositions should contain 0.1% to 80% by weight of active ingredient, especially when in tablet form.

The dose employed depends upon the desired antimalarial effect, the route of administration and the duration of the treatment. In the adult, the doses are generally between 0.01 and 100 mg (preferably between 0.01 and 1.0 mg) of compound of formula II per kg body weight per day, and optionally together with between 1.0 and 50 mg (preferably between 1.0 and 10 mg) of another antimalarial compound or another therapeutic agent per kg body weight per day by oral administration.

The compounds of formula II may be administered each day or, according to the wishes of the medical or veterinary practitioner, less often, e.g. weekly.

The present invention provides a method of treating or preventing malaria in man and other warm-blooded animals which comprises administering to the human or animal an amount of a compound or compounds of formula II sufficient to combat a malarial infection.

The present invention further provides a method of treating or preventing malaria in man and other warm-blooded animals which comprises administering to the human or animal an amount of a compound or compounds of formula II and another antimalarial compound or another therapeutic agent sufficient, in combination, to combat a malarial infection.

The following Composition Example illustrates pharmaceutical compositions according to the present invention.

COMPOSITION EXAMPLE

Capsules for oral administration were made up in the usual manner by filling No. 2 size gelatin capsules each with 155 mg of the following composition:

2,4-diamino-5-[3-{4-(4-chlorophenyl)phenoxy]-propoxy]-6-methylpyrimidine monohydrochloride—50 mg
potato starch—100 mg
magnesium stearate—2.5 mg
Aerosil (a registered Trade Mark)—2.5 mg

We claim:

1. A pyrimidine derivative of the formula:

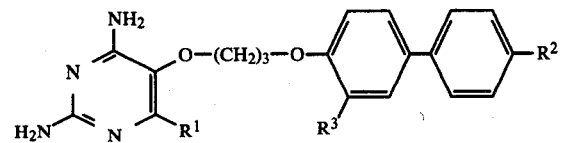

wherein $R^1$ represents methyl or ethyl, $R^2$ represents bromine or chlorine, and $R^3$ represents hydrogen, chlorine, bromine or iodine, or alkyl of 1 through 4 carbon atoms, alkenyl of 2 through 4 carbon atoms, cyano or trifluoromethyl, and its pharmaceutically acceptable acid addition salts.

2. A pyrimidine derivative according to claim 1 which is 2,4-diamino-5-[3-{4-(4-chlorophenyl)-phenoxy}propoxy]-6-methylpyrimidine and its pharmaceutically acceptable acid addition salts.

3. A pyrimidine derivative according to claim 1 which is 2,4-diamino-5-[3-{2-bromo-4-(4-bromophenyl)phenoxy}propoxy]-6-methylpyrimidine and its pharmaceutically acceptable acid addition salts.

4. A pharmaceutical composition which comprises, as active ingredient, an antimalarially effective amount of a pyrimidine derivative of the formula depicted in claim 1, or a pharmaceutically acceptable salt thereof, in association with a pharmaceutically acceptable carrier.

5. A method of treating or preventing malaria in man or other warm-blooded animal which comprises administering to the human or other animal an amount of a pyrimidine derivative of the formula depicted in claim 1, or a pharmaceutically acceptable acid addition salt thereof, sufficient to combat, or prevent, a malarial infection.

6. A method of treating or preventing malaria in a human adult according to claim 5 which comprises administering to the human adult a dose of between 0.01 and 100 mg of a pyrimidine derivative of the formula depicted in claim 1, per kg body weight per day sufficient to combat, or prevent, a malarial infection.

* * * * *